United States Patent [19]

Steenhuisen et al.

[11] Patent Number: 4,801,012

[45] Date of Patent: Jan. 31, 1989

[54] HOLDER FOR A PLURALITY OF SYRINGES

[75] Inventors: Johannes E. Steenhuisen; Gerrit Grotenhuis, both of Olst, Netherlands

[73] Assignee: Duphar International Research B.V., Weesp, Netherlands

[21] Appl. No.: 70,391

[22] Filed: Jul. 7, 1987

[30] Foreign Application Priority Data

Jul. 10, 1986 [NL] Netherlands .................. 8601799

[51] Int. Cl.$^4$ ............................................. B65D 83/10
[52] U.S. Cl. ...................................... 206/366; 206/480
[58] Field of Search ............... 206/363, 364, 365, 366, 206/477, 478, 480, 481, 485

[56] References Cited

U.S. PATENT DOCUMENTS

| | | | |
|---|---|---|---|
| 899,664 | 5/1908 | Goodrich | 206/477 X |
| 934,486 | 5/1909 | Walling | 206/366 |
| 2,472,028 | 5/1949 | Son | 206/365 |
| 3,255,873 | 6/1966 | Speelman | 206/366 |
| 3,439,796 | 4/1969 | Zykoski | 206/366 |
| 3,727,749 | 4/1973 | Martin | 206/366 |
| 3,768,635 | 10/1973 | Eggert | 206/366 |
| 3,923,152 | 12/1975 | Minneman | 206/478 X |
| 4,015,709 | 4/1977 | Millet | 206/366 |
| 4,119,204 | 10/1978 | Peckar | 206/480 X |
| 4,572,371 | 2/1986 | Asenbauer | 206/480 X |

Primary Examiner—Joseph Man-Fu Moy
Attorney, Agent, or Firm—Stevens, Davis, Miller & Mosher

[57] ABSTRACT

The invention relates to a holder for a plurality of disposable syringes, the syringes comprising a barrel, a needle connection means on the front end of the barrel, in which or to which an injection needle is or can be sealingly connected, and a finger grip, provided with an outwardly projecting flange and optionally with a clamping sleeve for a clamping connection around the rear open end of the barrel. The holder comprises a strip of flexible material one side of which comprises a number of resilient projections, distributed over the surface, for a detachable connection of the syringes in such a way that the rear end of the barrel or the rear face of the finger grip adjoins the surface of the strip in a non-sealing manner.

12 Claims, 3 Drawing Sheets

HOLDER FOR A PLURALITY OF SYRINGES

The invention relates to a holder for a plurality of disposable syringes, the syringes comprising a barrel, a needle connection means on the front end of the barrel, in which or to which an injection needle is or can be sealingly connected, and a finger grip, provided with an outwardly projecting flange and optionally with a clamping sleeve for a clamping connection around the rear open end of the barrel.

Such a holder is known and is used generally as a component of a package for syringes. Because it is of advantage to pack the syringes in sterile manner, the holder is usually constructed in such a way that the syringes can be sealingly connected to the holder or accommodated in the holder. A device for connecting and sealing a plurality of syringes in a sterile manner is described, for example, in U.S. Pat. No. 3,255,873.

However, the user of the syringes often desires the possibility of (post)sterilising the syringes so as to be absolutely sure that the syringes will be sterile when an injection is administered. When a holder sealing the syringes in a sterile manner is used as described hereinbefore, said user must first detach the syringes from or out of the holder in order to be able to sterilise them.

It is the object of the present invention to provide a holder for syringes which permits of a sterilisation of the syringes without it being necessary to detach the syringes from the holder.

This object can be achieved by means of a holder of the type mentioned in the opening paragraph, which holder is characterised according to the invention in that it comprises a strip of a flexible material, one side of which comprises a number of resilient projections, distributed over the surface, for a detachable connection of the syringes in such a way that the rear end of the barrel or the rear face of the finger grip adjoins the surface of the strip in a non-sealing manner.

Since the syringes are connected to the holder in a non-sealing manner, the holder with syringes can be accommodated entirely in a device suitable for sterilisation, for example, a steam sterilizer, so as to sterilise the syringes. Optionally, the holder with syringes may then be packaged in a sterile manner, for example, in a sealing blister pack known for this purpose.

In German Patent Application (Offenlegungsschrift) No. 2742253 a holder for syringes is described consisting of a profiled member having a C-shaped cross-section on which a plurality of syringes can be connected by inserting them into the profiled member by means of an end collar. Such a holder is not suitable either for the object of the present invention because with a clamping connection the rear open end of the syringes will easily be sealed by the holder, as a result of which steam sterilisation of the syringes will be prevented, while with a non-clamping connection in which sterilization is possible indeed, the syringes will slide out of the holder too easily when handling the holder. Moreover, the syringes are connected on this known holder in a fundamentally different manner, as a result of which the connection and detaching of the syringes is impeded in small spaces, for example, the sterile room in which, for example, the dispensing of the not yet prefilled syringes should be carried out.

The strip is preferably manufactured from a flexible synthetic material, for example, polypropylene, The resilient projections are preferably made of the same synthetic material and may then be formed integral with the strip. Such an integrally manufactured holder can be made, for example, by injection moulding from the desired synthetic material.

To additionally ensure that the syringes after connection to the holder cannot sealingly adjoin the surface of the strip and thus prevent sterilization of the syringes, the holder at the side holding the projections comprises a longitudinal spacing ridge, which is smaller then the rear aperture of the barrel of the syringes to be connected.

In a preferred embodiment of the holder of the invention, each projection has such dimensions, that the syringe can be connected around the projection on the strip with its rear open end of the barrel or with the rear aperture of the clamping sleeve of the finger grip.

In a suitable embodiment the last-mentioned holder is destined for the connection of syringes in which the rear open end of the barrel internally comprises a radially inwardly projecting circumferential end edge, or in which such an end edge is formed by the rear aperture of the clamping sleeve of the finger grip clamped around the rear end of the barrel. A holder destined for such syringes is preferably characterised in that each projection comprises an end portion having an entirely or substantially cylindrical outer surface having a diameter slightly larger than the end edge on the inner wall of the barrel or of the clamping sleeve, which end portion is connected to the strip via a portion having a reduced diameter, the portion of reduced diameter having at least the same length as the said end edge. In this manner a good connection of the syringes on the holder is ensured and, when it is provided that the rear end of the barrel or the rear face of the finger grip of the syringes to be connected does not sealingly adjoin the surface of the strip, sterilisation of the syringes after connection on the holder cannot be impeded. An example of a syringe comprising a finger grip with clamping sleeve is disclosed in U.S. Pat. No. 4,235,235. Of course, many other single or multiple-chamber syringes are known which are suitable for being connected on the holder according to the invention.

The resilient projections may be annular, so have a fully closed outer surface, connected to the strip by means of a portion of reduced diameter. However, in a favourable embodiment of the projections have a non-fully closed outer surface; as a result of this the resilience is favoured so that the connection of the syringes on the holder is facilitated. In such an embodiment, each projection comprises at least two cam-shaped elements which are proportioned so that, upon connecting and detaching the syringe, they can be bent resiliently towards each other to allow their end portions to pass the end edge on the inner wall of the barrel or of the clamping sleeve; the number of cam-shaped elements is preferably 3, 4 or 5.

In order to allow easy connection of the syringes on the holder and easy detachment from the holder, the projections are preferably provided on the strip in one straight line. In this manner, the holder with syringes connected thereon can also be placed more easily in a sterilization device.

In an equally preferred embodiment of the holder of the invention, the projections are provided in pairs in such mutual distances at the side edges of the strip, that the flange of the finger grip of the syringe can be connected between each pair of projections. In this way a very suitable connection of the syringes is obtainded, while the syringes can be detched easily by exerting a backward force, i.e. a force directed away from the strip, on the syringes. In said last embodiment preferably each projection comprises a resilient pawal which is perpendicularly provided on the surface of the strip and comprises an inwardly projecting end edge for connecting the flange of the finger grip. Further it is of advantage that the holder at the side holding the projections comprises a number of spacers, distributed over the surface, to maintain the syringes after connection on the holder in spaced relationship from each other.

To allow an easy introduction of the holder with syringes connected thereon into a sterilization device, the strip of the holder preferably comprises finger grips at its both ends, for example, in the form of faces comprising upright edges and having approximately the size of the finger tips.

The holder is destined not only for connecting pre-filled syringes, that is to say syringes already filled with injections liquid, which can be subjected to a post-sterilization while being connected on the holder, but also, and that in particular, for the connection of pre-fillable syringes. Prefillable syringes are to be understood to mean syringes which are supplied by the manufacturer in an empty condition and are filled with injection liquid afterwards and are then marketed. The empty syringes which are supplied while being connected on the holder can now be placed into a sterilization device, for example, a stream sterilizer, and can be sterilised. The holder permits a simple introduction into a dispensing device in which the syringes are usually dispensed with injection liquid by machine. There the syringes can be detached from the holder under sterile conditions, preferably mechanically and all at a time, can be dispensed with one or more injection liquids and, after having placed the pistons, can be connected again on the holder. Finally, the holder with the filled syringes can be packaged in a sterile manner, optionally after a post-sterilization. In this manner the same holder may be used during various phases of the production process.

The invention will now be described in greater detail with reference to preferred embodiments which are shown in the drawings, in which.

Figures 3, 4:
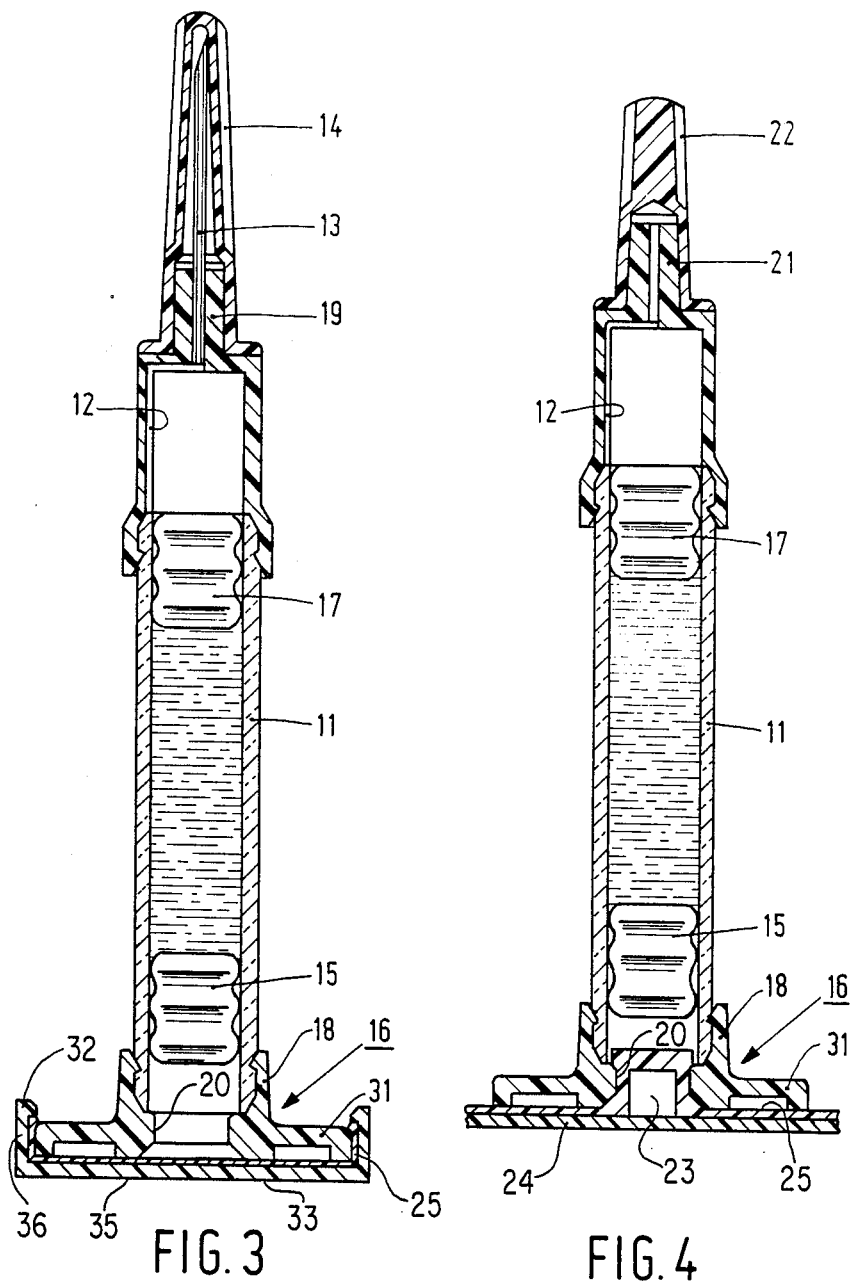
Figure 5:
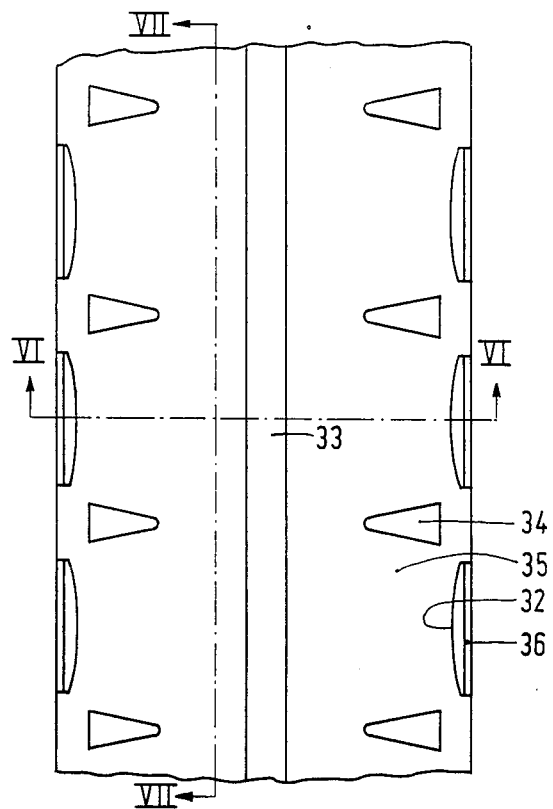
FIG. 5 is a plan view of a part of a holder for syringes according to the invention, in a different embodiment.
Figure 6:
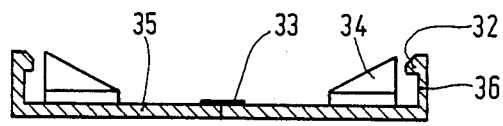
FIG. 6 is a cross-sectional view of the FIG. 5 holder, taken on the line VI—VI in FIG. 5.
Figure 7:
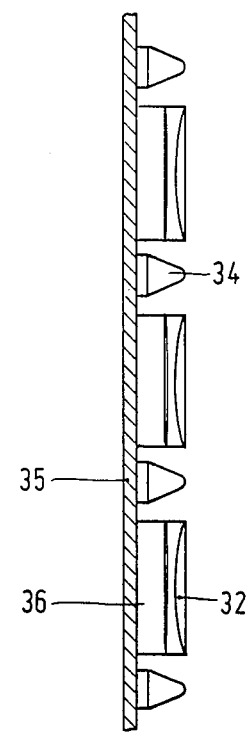

FIG. 7 is a longitudinal sectional view of the part of the holder shown in FIG. 5, namely taken on the line VII—VII in FIG. 5; and FIGS. 3 and 4 are longitudinal sectional views of prefilled syringes which can be connected on the holder shown in FIGS. 1 and 2, and 5–7 respectively.

The syringe shown in FIG. 3 comprises a barrel 11 in one end of which a piston 15 is provided and at the other end of which an injection needle 13 covered in a sterile manner by a needle guard 14 is connected by means of a needle holder 19. In order for the injection liquid, enclosed between the piston and a stopper 17 in the barrel, to reach the injection needle during use of the syringe, one or more grooves 12 are recessed in the inner wall of the needle holder, broadly as described in the U.S. Pat. No. 4,235,235 mentioned hereinbefore, The syringe shown in FIG. 4 does not comprise an injection needle upon delivery, but comprises a needle holder 21 having a neck whose outer surface is in the form of a truncated cone and around which the separately supplied injection needle having a cap can be connected in a tightly fitting manner; a Luer cone or a Luer lock cone is often used for such a connection. Before use the neck of the needle holder 21 is sealed in a sterile manner by means of a protecting cap 22. At the end remote from the needle or needle connection the barrel comprises a finger grip 16 which is provided with an outwardly projecting flange 31 and firmly connected to the rear edge of the barrel by means of a clamping sleeve 18. If desired, the clamping sleeve may internally comprise a radially inwardly projecting circumferential edge which engages in a circumferential groove recessed in the outer wall of the barrel. This provision, shown in FIGS. 3 and 4 and also termed snap connection, ensures a firm locking of the finger grip on the barrel. As is shown in FIGS. 3 and 4, the rear edge of the barrel engages an end edge 20 which is formed by the rear aperture of the clamping sleeve 18 and which projects slightly inwardly, that is to say with a smaller diameter that the inner diameter of the barrel. In a pre-fillable syringe the piston 15 and the injection liquid between the piston and the stopper 17 are not present.

Figures 1, 2:
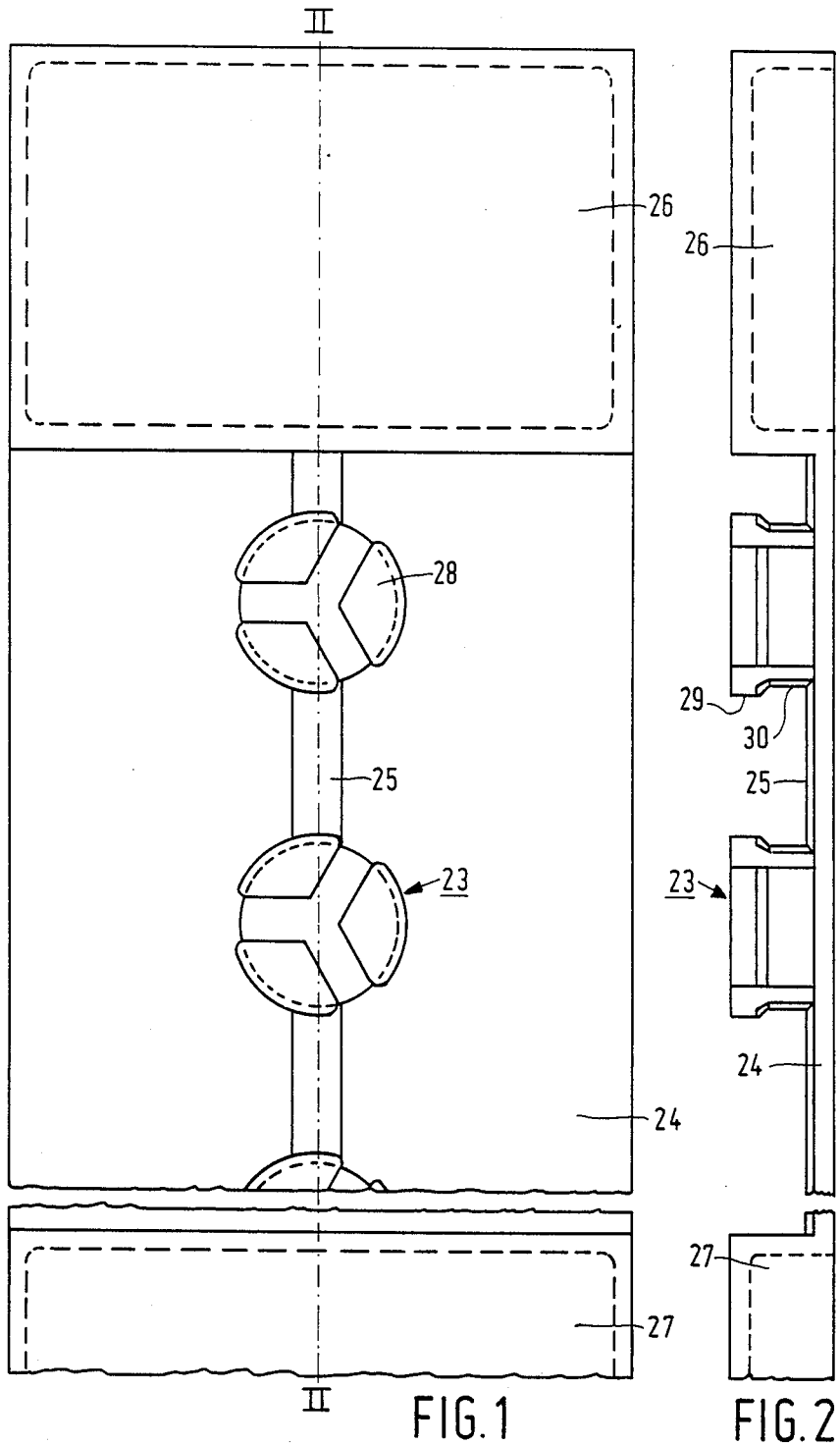
FIG. 1 is plan view of a part of a holder for syringes according to the invention.
FIG. 2 is a longitudinal sectional view of the part of the holder shown in FIG. 1, namely taken on the line II—II in FIG. 1.

The holder, a part of which is shown in the plan view of FIG. 1 and in the longitudinal sectional view of FIG. 2, comprises a plurality of, for example, twenty-five, projections 23 which are provided on a strip 24 in one straight line. A longitudinal ridge 25 is present between the projections and the strip and additionally ensures that the syringes connected to the holder cannot sealingly adjoin the surface of the strip. The strip comprises finger grips 26 and 27 on each end which consist of surfaces approximately the size of the finger tips and circumferentially comprise upright edges. The strip and the projections on the strip have been manufactured integrally, for example, by injection moulding, from a flexible material, for example, from a suitable synthetic material such as polypropylene. Each projection comprises three cam-shaped elements 28 having an end portion 29 together constituting a substantially cylindrical outer surface, and having a portion of reduced diameter 30 which is connected to the strip. It is to be noted that the syringes shown in FIGS. 3 and 4 are not drawn to the same scale as the holder of FIGS. 1 and 2. The diameter of the substantially cylindrical outer surface of the end portions 29 of the cam-shaped elements 28 is slightly larger than the end edge 20 formed by the rear opening in the clamping sleeve 18 of the finger grip in the syringes shown in FIGS. 3 and 4. When connecting one of these syringes to a projection 23 of the holder shown in FIGS. 1 and 2, the cam-shaped elements 28 slightly bend towards each other so that the end portions 29 can paass the end edge 20. After passing the end edges, the cams bend apart again as a result of their resilience till against the inner wall of the barrel, the end edge 20 of the syringe engaging in the portions of the reduced diameter 30 of the cam-shaped elements 28. In the same manner the syringe can be taken from the holder easily be exerting on the syringe a force directed away from the holder.

The holder, a part of which is shown in FIGS. 5–7, comprise a plurality of projections 36, placed in pairs at the side edges of the strip 35 of the holder. The strip comprises a longitudinal ridge 33 between the pairs of projections, additionally ensuring that the syringes connected to the holder cannot sealingly adjoin the surface of the strip. The strip may comprise finger grips, not shown in the Figures, on each end, as described in the FIGS. 1-2 embodiment. The strip further comprises a number of spacers 34, distributed over the surface. The holder has been manufactured integrally, e.g. as the holder of FIGS. 1-2, described hereinbefore. Each projection 36 comprises a resilient pawl-like element which is perpendicularly provided on the surface of the strip and an inwardly projecting end edge 32. The spacers, having a basis with a substantially triangular cross-section, taper upwards. The syringes shown in FIGS. 3 and 4 are equally not drawn to the same scale as the holder of FIGS. 5-7. When connecting one of the syringes to the holder shown in FIGS. 5-7, the projections 36 slightly bend outwards to allow the outer edge of the flange 31 of the syringe finger grip to pass the inwardly projecting edges 32 of a pair of projections 36 on both sides of the strip. Each syringe fits with its finger grip between four spacers 34; these spacers maintain the connected syringes in spaced relationship from each other. After passage of the end edges 32, the projections move in their original position as a result of their resilience, the outer edge of the flange of the finger grip of the syringe engaging in the pawl-like elements of the projections 36. In the same manner the syringe can be taken from the holder easily by exerting on the syring a force directed away from the holder.

We claim:

1. A holder for a plurality of disposable syringes, the syringes comprising a barrel having a front end and a rear aperture, on the front end of the barrel a needle connection means for sealingly connecting an injection needle, and a finger grip, provided with an outwardly projecting flange, which holder is characterized in that it comprises a strip of flexible material, one side of which comprises a number of resilient projections, distributed over the surface, for a detachable connection of the syringes in such a way that the rear face of the finger grip adjoins the surface of the strip in a non-sealing manner, and in that it comprises at the side holding the projections a longitudinal spacing ridge, which is smaller than the rear aperture of the barrel of the syringes to be connected.

2. A holder as claimed in claim 1, characterised in that each projection has such dimensions, that the syringe can be connected around the projection on the strip with its rear open end of the barrel or with the rear aperture of the clamping sleeve of the finger grip.

3. A holder as claimed in claim 2 for connecting syringes in which the rear open end of the barrel internally comprises a radially inwardly projecting circumferential end edge or in which such an end edge is formed by the rear aperture of the clamping sleeve of the finger grip clamped around the rear end of the barrel, which holder is characterised in that each projection comprises an end portion having an entirely or substantially cylindrical outer surface having a diameter which is slightly larger than the end edge on the inner wall of the barrel or of the clamping sleeve, which end portion is connected to the strip via a portion having a reduced diameter, the portion of reduced diameter being at least as long as the said end edge.

4. A holder as claimed in claim 3, characterised in that each projection comprises at least two cam-shaped elements which are proportioned so that, when connecting and detaching the syringe, they can resiliently be bent towards each other to allow their end portions to pass the end edge on the inner wall of the barrel or of the clamping sleeve.

5. A holder as claimed in any of the preceding claims 2-4, characterized in that the projections are provided on the strip in one straight line.

6. A holder as claimed in claim 1, characterised in that the projections are provided in pairs in such mutual distances at the side edges of the strip, that the flange of the finger grip of the syringe can be connected between each pair of projections.

7. A holder as claimed in claim 6, characterised in that each projection comprises a resilient pawl which is perpendicularly provided on the surface of the strip and comprises an inwardly projecting end edge for connecting the flange of the finger grip.

8. A holder as claimed in claim 6 or 7, characterised in that the holder at the side holding the projections comprises a number of spacers, distributed over the surface, to maintain the syringes after connection on the holder in spaced relationship from each other.

9. A holder as claimed in claim 1, characterised in that the strip comprises finger grips at its both ends.

10. A holder as claimed in claim 6 and holding a plurality of disposable syringes, wherein the holder comprises a strip of flexible material, one side of which comprising a number of resilient projections, distributed over the surface, said projections being provided in pairs at the side edges of the strip in such mutual distances, that the syringes are connected to the strip with the flange of their finger grips between each pair of projections in such a way, that the rear face of the finger grips adjoin the surface of the strip in a non-sealing manner, a longitudinal ridge on the strip spacing the connected syringes from the surface of the strip.

11. A holder holding a plurality of disposable syringes as claimed in claim 10, wherein said projection comprises a resilient pawl which is perpendicular provided on the surface of the strip and comprises an inwardly projecting end edge to engage the flange of the finger grip of a syringe connected on the holder.

12. A holder holding a plurality of disposable syringes as claimed in either claim 10 or claim 11, wherein the syringes are connected on the holder in spaced relationship from each other by means of a number of spacers, distributed over the surface of the strip.

* * * * *